United States Patent
Onikienko et al.

(10) Patent No.: US 9,616,100 B2
(45) Date of Patent: Apr. 11, 2017

(54) METHODS OF USE OF HSP70 FOR INCREASED PERFORMANCE OR TREATMENT OF HSP70 RELATED DISORDERS

(71) Applicants: Sergei B Onikienko, St. Petersburg (RU); Alex Nivorozhkin, West Roxbury, MA (US); Alexander V Zemlyanoi, St. Petersburg (RU)

(72) Inventors: Sergei B Onikienko, St. Petersburg (RU); Alex Nivorozhkin, West Roxbury, MA (US); Alexander V Zemlyanoi, St. Petersburg (RU)

(73) Assignee: ALTERNATIVE INNOVATIVE TECHNOLOGIES LLC, West Roxbury, MA (US)

( * ) Notice: Subject to any disclaimer, the term of this patent is extended or adjusted under 35 U.S.C. 154(b) by 0 days.

(21) Appl. No.: 14/333,483

(22) Filed: Jul. 16, 2014

(65) Prior Publication Data

US 2014/0329764 A1 Nov. 6, 2014

Related U.S. Application Data

(63) Continuation of application No. 13/536,542, filed on Jun. 28, 2012, now abandoned.

(60) Provisional application No. 61/502,332, filed on Jun. 28, 2011.

(51) Int. Cl.
*A61K 38/17* (2006.01)
*A61K 47/48* (2006.01)

(52) U.S. Cl.
CPC .......... *A61K 38/17* (2013.01); *A61K 38/1703* (2013.01); *A61K 47/48215* (2013.01)

(58) Field of Classification Search
None
See application file for complete search history.

(56) References Cited

U.S. PATENT DOCUMENTS 5,348,945 A * 9/1994 Berberian .............. A61K 38/16
514/1.9
2011/0286993 A1* 11/2011 Jensen ................... A61K 38/17
424/94.6

FOREIGN PATENT DOCUMENTS

WO WO 2009155936 A1 * 12/2009

OTHER PUBLICATIONS

Flerov et al. The use of HSP70 for prevention of consequences of unavoidable stress in rats. Bull Exp Biol Med. Aug. 2003;136(2):120-2.*
Gifondorwa et al. Exogenous delivery of heat shock protein 70 increases lifespan in a mouse model of amyotrophic lateral sclerosis. J Neurosci. Nov. 28, 2007;27(48):13173-80.*
Kustanova et al. Exogenous heat shock protein 70 mediates sepsis manifestations and decreases the mortality rate in rats. Cell Stress Chaperones. 2006 Autumn;11(3):276-86.*
Lee et al. Controlled delivery of heat shock protein using an injectable microsphere/hydrogel combination system for the treatment of myocardial infarction. J Control Release. Aug. 4, 2009;137(3):196-202. Epub Apr. 14, 2009.*
Pasut et al. Protein, peptide and non-peptide drug PEGylation for therapeutic application. Expert Opin. Ther. Patents (2004)14(6):859-894.*
U. S. Appl. No. 13/651,416, filed Oct. 13, 2012.*
Morton et al. The exercise-induced stress response of skeletal muscle, with specific emphasis on humans. Sports Med. 2009;39(8):643-62. doi: 10.2165/00007256-200939080-00003.*

* cited by examiner

*Primary Examiner* — David Romeo
(74) *Attorney, Agent, or Firm* — JWIP & Patent Services, LLC; Jacob G. Weintraub, Esq.

(57) ABSTRACT

The present invention relates to novel therapies that utilize exogenous HSP70 for the treatment of disorders or conditions regulated by HSP70 through administration of exogenous HSP70.

5 Claims, 4 Drawing Sheets

METHODS OF USE OF HSP70 FOR INCREASED PERFORMANCE OR TREATMENT OF HSP70 RELATED DISORDERS

RELATED APPLICATIONS

This application is a continuation of U.S. application Ser. No. 13/536,542, filed Jun. 28, 2012, which claims the benefit of priority from U.S. Provisional Patent Application No. 61/502,332, filed on Jun. 28, 2011, each of which is incorporated herein by reference in their entirety.

BACKGROUND OF THE INVENTION

Over 6 million Americans are diagnosed annually with musculoskeletal disease, which is a major cause of work disability. Annual costs associated with treatment and care of musculoskeletal disease is in the tens of billions of dollars. Muscle degeneration and impairment in such disease may be stemming from various causes, including tissue ischemia, severe injury, advanced age, and muscular dystrophy resulting form genetic defects as well as major diseases such as cancer or kidney failure.

Current key therapeutic approaches and standards of care are typically limited to physiotherapeutic rehabilitation, pain management and anti-inflammatory medications. Lately, there has been an increased interest in developing new interventions focused directly on muscle regeneration. For example, some promise was shown by using cell therapies and related muscle progenitor cells injected directly or as a part of the polymer scaffold (Levenberg et al. 2005). However, this approach is limited by poor integration of the transplanted cells and their low survival.

Growth factors have also been extensively explored in context of ischemic vascular regeneration (Silva et al., 2007), and more recently extended to muscular regeneration (Messina et al., 2007; Kärkkäinen et al., 2009). It is notable that most of the work was done with a vascular endothelial growth factor VEGF, a well-known proangiogenic regulator and thus it was challenging to separate angiogenic contributions from direct effects on muscle development and evolution of the related progenitor cells population. However, in a recent article Borselli et al. (Borselli et al., 2010) showed a synergistic effect of VEGF and an insulin growth factor IGF-1 that binds to type I receptors and may activate several intracellular signaling pathways including the MAP kinase, PI3-K, and the calcium-calmodulin-dependent protein kinase pathway; and therefore lead to the activation and proliferation of the satellite cells, their terminal myogenic differentiation, increased protein synthesis, and myofiber survival. In this respect, it was shown that a sustained-release alginate formulation of both singular agents and their combination was much more effective than bolus administration.

Additional therapeutic approaches have looked into heat shock protein 70 (HSP70), one of several proteins in the general class of heat shock proteins (HSPs). HSP70 has been implicated in many processes including folding and unfolding of nascent proteins, activation of a multi-enzymatic complex, and protein transport. Additionally, HSPs are important for the maintenance of cell integrity during normal growth as well as during pathophysiological conditions (Vigh et al. 1997). It has been shown that tissue injury, whether caused by surgery, trauma or disease, results in the induction of heat shock/stress proteins. An inducible form of the 70 kDa heat shock protein family HSP72 has been detected intra- and extra-cellularly in different organs, including skeletal muscles in response to exercise.

The biological significance of these processes appears to be related: to aid cell survival and chaperone misfolded and denatured proteins. As molecular chaperones, HSPs are also fundamental in facilitating cellular remodeling processes inherent to the training response (Morton et al. 2009; Whitman et al. 2008). Moreover, the beneficial effects of HSPs have been implicated in a number of different diseases such as diabetes; wound healing (Atalay et al. Curr. Pep. Prot. Sc. 2009; 10:85); cancer (Ciocca et al., Stress Cell Chap. 2005; 10:86; Guzhova et al. Tsitologia 2005, 47:187); sepsis (McConnell et al.; J. Immun. 2011; 186:3718; Kustanova et al. Cell Stress Chap. 2006; 11:276); cardiac injury (Knowlton et al. Am. J. Physiol. Heart Cir. Physiol. 2001; 280: H455); muscular injury and degeneration; recovery from physical and exercise stress (Morton et al. Sports Med. 2009; 39(8):643); neuro-degeneration including Parkinson disease, Alzheimer disease, Huntington disease, amyotrophic lateral sclerosis (Turturici et al., Biochem. Res. Int. 2011); spinal cord injury (Reddy et al. Neurosurg. Focus 2008, 25(5):1); traumatic brain injury; stroke; eye neurodegenerative diseases including glaucoma and macular degeneration (Levin, Surv. Ophthalm. 2003; 48:S21); and epilepsy (Ekimova et al. J. Neurochem. 2010; 115:1035).

At the same time, it has been found that patients with chronic fatigue syndrome (CFS) present an accentuated exercise-induced oxidative stress. Compared with controls, resting CFS patients had low levels of HSP70 and delayed and marked reduction of HSP70 levels in response to maximal exercise (Jammes et al. 2009). In this regard, HSP70 has been implied as a main mediator of the phytoadaptogens such as *Rhodiola rosea* and *Eleutheroccocus senticosus* that improve attention, cognitive function and mental performance in fatigue and chronic fatigue syndrome as well as increase endurance. HSP70 inhibits the expression of the NO synthase II and affects the levels of circulating cortisol via direct interaction with glucocorticoid receptors and JNK pathway. Consequently, prevention of the stress-induced NO and associated decrease in ATP production result in increased performance and endurance (Panossian et al. 2009). Additionally, in HSP70 inhibition (by siRNA interference and a small molecule, N-formyl-3,4-methylene-dioxy-benzylidene-butyrolactam, KNK-437) models of vascular insufficiency (Shiota et al. 2010), the lack of HSP70 was linked to disruption of the VEGF-related pathways and Akt activation specifically.

In an effort to capitalize on the involvement of HSP70 in many of these disorders or conditions, several patent applications have reported the utility of HSPs in relation to the recovery from injury (Slepian, U.S. Pat. No. 5,914,345; Srivastava, US Patent Application US 2003/0012793). Additional applications have focused on compounds that induce HSP70, such as geranylgeranylacetone, which have been described to protect subjects from the effect of ischemic-reperfusion injury (Takahashi N, U.S. Pat. No. 6,846,845 B2). Moreover, BGP-15, a pharmacological inducer of Hsp72 (currently in clinical trials for diabetes), has been shown to improve muscle architecture, strength, and contractile function in severely affected diaphragm muscles in two dystrophic mice models relevant to Duchenne muscular dystrophy (Gehrig et al., 2012).

Although evidence has suggested the role of HSP70 in certain indications, current treatments that have adopted strategies to control in vivo HSP70 production have not met the need in this arena. As such, there is strong need for novel therapies that address this current demand.

SUMMARY OF THE INVENTION

Accordingly, the present invention relates to novel therapies that utilize HSP70 for the treatment of disorders or conditions regulated by HSP70 through administration of exogenous HSP70. In this regard, the present invention provides formulations of HSP70 that offer therapeutic effectiveness in the treatment of HSP70 related disorders or conditions. Furthermore, the present invention is directed to methods comprising the administration of exogenous HSP70 for use in the treatment of HSP70 related disorders or conditions, for example, for increased performance capability, e.g., physical and mental, increased endurance, or alleviating fatigue syndrome. In a particular example, the HSP70 related disorder or condition may be muscle degeneration and impairment stemming from various causes including tissue ischemia, severe injury, exercise-induced tissue injury and fatigue, advanced age, muscular dystrophy resulting form genetic defects and also caused by major diseases such as cancer, kidney failure and others.

Thus, in one aspect, the invention provides a formulation comprising HSP70, e.g., a therapeutically effective amount of HSP70, and pharmaceutically acceptable carrier.

In another aspect, the invention provides a method of treatment of an HSP70 related disorder or condition, wherein the method comprises administering to a subject a compound of the present invention, e.g., a therapeutically effective amount of HSP70, such that the HSP70 related disorder or condition is treated in the subject.

In another aspect, the invention provides a method to increase performance (e.g., endurance), alleviate a fatigue syndrome, or treat muscle damage or muscle degeneration comprising administering to the mammal a compound of the invention, e.g., a therapeutically effective amount of HSP70, e.g., human heat shock protein 70, such that performance (e.g., endurance) is increased, the fatigue syndrome is alleviated, or the muscle damage or muscle degeneration is treated in the mammal.

DETAILED DESCRIPTION OF THE INVENTION

Figure 1:
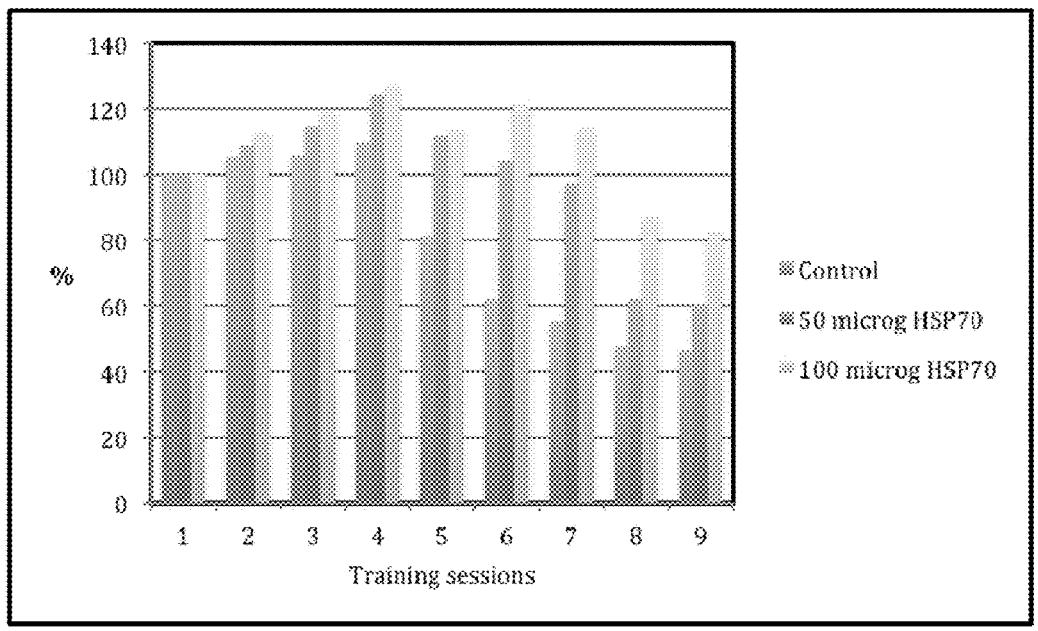
FIG. 1 depicts the variations in endurance (time of exercise to exhaustion) relative to the result of the first exercise session.

The present provides a novel therapy for treatment of HSP70 related disorders or conditions. In particular, the present invention is directed to HSP70, or formulations thereof, and the administration of such for use in the treatment of HSP70 related disorders or conditions. The present invention, including compounds, methods, and pharmaceutical compositions will be described with reference to the following definitions that, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

As used herein, the term "HSP70" or "heat shock protein 70, " which are used interchangeably herein, describes an exogenously derived heat shock protein characterized by its association with the art-recognized family of 70 kiloDalton heat shock proteins, the structures of which are well-known in that art. In addition, as used herein, the term "HSP70" covers native HSP70, recombinant HSP70, as well as derivatives thereof, e.g., PEG-HSP70.

As used herein, "HSP70 related disorders or conditions" describes the class of conditions or disorders that are regulated by HSP70. Exemplary HSP70 related disorders or conditions include, but are not limited to myopathy, both congenital such as muscle dystrophies, and acquired such as rhabdomyolysis, polymyositis, and dermatomyositis; acute trauma; traumatic toxicosis due to crash injury; ischemia-reperfusion injury including stroke and myocardial infarction; heart failure; muscle damage as a result of the excessive physical exercise, e.g., without anabolic effects such as increase in body mass; cancer; neurodegenerative diseases such as Alzheimer's, Huntington's, Parkinson's, and Amyotropic lateral sclerosis; certain inflammation; reduced physical performance (e.g., endurance), e.g., relative to absolute capability of individual; reduced mental performance, e.g., relative to absolute capability of individual; fatigue syndrome; sleep deprivation; sepsis; and hemorrhagic shock. In a particular example, the HSP70 related disorder or condition may be muscle degeneration and impairment stemming from various causes including tissue ischemia, severe injury, exercise-induced tissue injury and fatigue, advanced age, muscular dystrophy resulting form genetic defects and also caused by major diseases such as cancer, kidney failure and others.

As used herein, the term "exogenous" describes the external origin of the HSP70, or alternatively stated, the exogenous HSP70 described herein, is derived or developed from outside the subject, e.g., through recombinant methods.

As used herein, the term "endurance" describes the ability to sustain a physical activity, perform repetitive submaximal contractions, or exert a force for a prolonged period. In certain embodiments, endurance may include aerobic endurance, anaerobic endurance, speed endurance, and strength endurance. In certain embodiments, increased endurance describes the ability to sustain the physical activity, contractions or force for a increased periods of time or with less exerted effort.

As used herein, the term "performance" describes the manner or quality of action taken, physically or mentally, to carry out a task. Increased mental or physical performance refers to the improved ability to carry out that task or multiple sequential tasks. Moreover, the compounds of the present invention are intended to affect improvement in physical performance or mental performance. In one embodiment the performance is physical performance. In certain embodiments where the performance is physical, the improved physical performance may include increased endurance, increased muscle power, or increased muscle strength. In another embodiment, the performance is mental performance. In certain embodiments where the performance is mental, the improved mental performance may include improved comprehension, improved memory retention, and improved mental acuity.

As used herein, and unless otherwise specified, the terms "treat," "treating" and "treatment" refer to the eradication or amelioration of a disease, disorder, or condition, or of one or more symptoms associated with the disease, disorder or condition. In certain embodiments, the terms refer to minimizing the advancement or worsening of the disease, disorder, or condition resulting from the administration of a compound of the invention to a patient with such a disease, disorder, or condition. In some embodiments, the terms refer to the administration of a compound provided herein, with or without other additional active agents, after the onset of symptoms of the particular disease, disorder, or condition. The terms "treating", "treatment", or the like, as used herein covers the treatment of a disease, disorder, or condition in a subject, e.g., a mammal, and includes at least one of: (i) inhibiting the disease, disorder, or condition, i.e., partially or completely halting its progression; (ii) relieving the disease, disorder, or condition, i.e. causing regression of symptoms of the disease, disorder, or condition, or ameliorating a symptom of the disease, disorder, or condition; and (iii) reversal or regression of the disease, disorder, or condition, preferably eliminating or curing of the disease, disorder, or condition. In a particular embodiment the terms "treating", "treatment", or the like, covers the treatment of a disease, disorder, or condition in a mammal, e.g., a primate, e.g., a human, and includes at least one of (i), (ii), and (iii) above. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, the terms "subject", and "patient" are used interchangeably. The terms "subject" and "patient" refer to an animal (e.g., a bird such as a chicken, quail or turkey) or a mammal including non-primates (e.g., a cow, pig, horse, sheep, rabbit, guinea pig, rat, cat, dog, and mouse) and primates (e.g., a monkey, chimpanzee and a human). In a particular embodiment, the subject is a human.

As used herein, and unless otherwise specified, the terms "prevent," "preventing" and "prevention" refer to the prevention of the onset, recurrence or spread of a disease, disorder, or condition, or of one or more symptoms thereof. In certain embodiments, the terms refer to the administration of HSP70 to a subject, with or without other additional active compounds, prior to the onset of symptoms, particularly to patients at risk of a disease, disorder, or condition provided herein. The terms encompass the inhibition or reduction of a symptom of the particular disease, disorder, or condition. Subjects with familial history of a disease, disorder, or condition, in particular, are candidates for preventive regimens in certain embodiments. In addition, subjects who have a history of recurring symptoms are also potential candidates for the prevention. In this regard, the term "prevention" may be interchangeably used with the term "prophylactic treatment." In certain embodiments, the prevention is achieved by administration of a prophylactically effective amount of a degradation resistant formulation of the invention.

As used herein, and unless otherwise specified, a "therapeutically effective amount" of an active agent, e.g., HSP70, is an amount sufficient to provide a therapeutic benefit in the treatment or management of a disease, disorder, or condition, or to delay or minimize one or more symptoms associated with the disease, disorder, or condition. A therapeutically effective amount of HSP70 means an amount of HSP70, alone or in combination with other therapies, which provides a therapeutic benefit in the treatment or management of the disease, disorder, or condition. The term "therapeutically effective amount" can encompass an amount that improves overall therapy, reduces or avoids symptoms or causes of disease, disorder, or condition, or enhances the therapeutic efficacy of another therapeutic agent.

As used herein, and unless otherwise specified, the terms "manage," "managing" and "management" refer to preventing or slowing the progression, spread or worsening of a disease, disorder, or condition, or of one or more symptoms thereof. Often, the beneficial effects that a subject derives from a prophylactic and/or therapeutic agent do not result in a cure of the disease, disorder, or condition. In this regard, the term "managing" encompasses treating a subject who had suffered from the particular disease, disorder, or condition in an attempt to prevent or minimize the recurrence of the disease, disorder, or condition.

As used herein, and unless otherwise specified, a "prophylactically effective amount" of an active agent, e.g., HSP70, is an amount sufficient to prevent a disease, disorder, or condition, or prevent its recurrence. A prophylactically effective amount of HSP70 means an amount of HSP70, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "polyethylene glycol" or "PEG" refers to a polyalkylene glycol compound or derivative thereof, with or without coupling agents or derivatization with coupling or activating moieties. In its typical form, PEG is a linear polymer with terminal hydroxyl groups and has the formula HO—CH$_2$CH$_2$—(CH$_2$CH$_2$O)$_n$—CH$_2$CH$_2$—OH. The number of repeating subunits "n" in the PEG is approximated for the molecular mass described in Daltons.

II. Compounds of the Invention

The compounds of the invention, HSP70 or derivatives thereof, may be used in the formulations and the methods of treatment of the invention. In certain embodiment, the invention provides formulations and methods of use of HSP70 in its native form. In certain embodiment, the invention provides formulations and methods of use of HSP70 in a derivatized form, e.g., pegylated (PEG-HSP70). In certain embodiment, the invention provides formulations and methods of use of recombinant HSP70, recombinant human HSP70 (rhHSP70). In certain embodiment, the invention provides formulations and methods of use of derivatized recombinant HSP70, pegylated recombinant human HSP70 (PEG-rhHSP70).

In one embodiment, the present invention provides an isolated HSP70, e.g., suitable for administration to a subject. In certain embodiments, the HSP70 is in enriched form, i.e., enriched HSP70, wherein the enriched HSP70 comprises HSP70 substantially free of non-HSP70 material. In specific embodiments, such enriched HSP70 is greater than 50% pure (or less than 50% non-HSP70 material), e.g., is greater than 60% pure, e.g., is greater than 70% pure, e.g., is greater than 80% pure, e.g., is greater than 90% pure, e.g., is greater than 92% pure, e.g., is greater than 94% pure, e.g., is greater than 96% pure, e.g., is greater than 98% pure, e.g., is greater than 99% pure.

III. Methods of the Invention

The invention relates to the method of use of a compound or formulations of the invention, which contain a heat shock protein 70, e.g., a recombinant human heat shock protein 70, for the treatment of HSP70 related disorders or conditions. For example, in one embodiment, the invention provides a method of treatment of an HSP70 related disorder or condition, wherein the method comprises administering to a subject, e.g., a mammal, a compound of the invention, e.g., a therapeutically effective amount of HSP70 (e.g., human heat shock protein 70, e.g., a formulation of human heat shock protein 70), such that the HSP70 related disorder or condition is treated in the subject.

In particular embodiments of the invention, the HSP70 related disorder or condition is selected from the group consisting of myopathy, both congenital such as muscle dystrophies, and acquired such as rhabdomyolysis, polymyositis, and dermatomyositis; acute trauma; traumatic toxicosis due to crash injury; ischemia-reperfusion injury including stroke and myocardial infarction; heart failure; muscle damage as a result of the excessive physical exercise, e.g., without anabolic effects such as increase in body mass; cancer; neurodegenerative diseases such as Alzheimer's, Huntington's, Parkinson's, and Amyotropic lateral sclerosis; certain inflammation; reduced physical performance (e.g., endurance), e.g., relative to absolute capability of individual; reduced mental performance, e.g., relative to absolute capability of individual; fatigue syndrome; sleep deprivation; sepsis; and hemorrhagic shock. In a particular example, the HSP70 related disorder or condition may be muscle degeneration and impairment stemming from various causes including tissue ischemia, severe injury, exercise-induced tissue injury and fatigue, advanced age, muscular dystrophy resulting form genetic defects and also caused by major diseases such as cancer, kidney failure and others.

In a specific embodiment, the HSP70 related disorder is sarcopenia, e.g., as associated with aging and the progressive decline of muscle mass, strength, and quality. In another specific embodiment, the HSP70 related condition is reduced physical performance (e.g., endurance), or reduced mental performance, wherein the performance (or endurance) is increased by treatment with the compounds of the invention. In another specific embodiment, the HSP70 related disorder is fatigue syndrome. In another specific embodiment, the HSP70 related disorder or condition is muscle damage or muscle degeneration. In another specific embodiment, the HSP70 related disorder or condition is cancer.

In another embodiment, the invention provides a method of treatment of an HSP70 related disorder or condition, wherein the method comprises administering to a subject a therapeutically effective amount of HSP70. These conditions include myopathy, both congenital such as muscle dystrophies, and acquired such as rhabdomyolysis, polymyositis, and dermatomyositis; acute trauma; traumatic toxicosis due to crash injury; ischemia-reperfusion injury including stroke and myocardial infarction; heart failure; muscle damage as a result of the excessive physical exercise, e.g., without anabolic effects such as increase in body mass; cancer; neurodegenerative diseases such as Alzheimer's, Huntington's, Parkinson's, and Amyotropic lateral sclerosis; certain inflammation; reduced physical performance (e.g., endurance), e.g., relative to absolute capability of individual; reduced mental performance, e.g., relative to absolute capability of individual; fatigue syndrome; sleep deprivation; sepsis; and hemorrhagic shock. In a specific embodiment, the HSP70 related disorder is sarcopenia, e.g., as associated with aging and the progressive decline of muscle mass, strength, and quality. In another specific embodiment, the HSP70 related condition is reduced physical performance (e.g., endurance), or reduced mental performance, wherein the performance (or endurance) is increased by treatment with a compound of the invention. In another specific embodiment, the HSP70 related disorder is fatigue syndrome. In another specific embodiment, the HSP70 related disorder or condition is muscle damage or muscle degeneration. In another specific embodiment, the HSP70 related disorder or condition is cancer.

In another embodiment, the invention provides a method to increase performance (e.g., endurance), alleviate fatigue syndrome, or treat muscle damage or muscle degeneration comprising administering to a subject, e.g., a mammal, a compound of the invention, e.g., a therapeutically effective amount of HSP70 (e.g., human heat shock protein 70, e.g., a formulation of human heat shock protein 70) such that performance is increased, the fatigue syndrome is alleviated, or the muscle damage or muscle degeneration is treated in the subject.

In another embodiment, the invention provides a method to increase performance (e.g., endurance), alleviate a fatigue syndrome, or treat muscle damage or muscle degeneration comprising administering to the mammal a formulation comprising human heat shock protein 70, such that performance is increased, the fatigue syndrome is alleviated, or the muscle damage or muscle degeneration is treated in the mammal.

In another embodiment, the invention provides a method to treat cancer comprising administering to the mammal a compound of the invention, e.g., a formulation comprising human heat shock protein 70, such that the cancer is treated in the mammal.

In certain embodiments of the invention, the HSP70 is recombinant human HSP70.

In certain embodiments of the invention, the HSP70 is pegylated HSP70.

In certain embodiments of the invention, the mammal is human.

In certain embodiments of the invention, the formulation is administered intravenously, subcutaneously, intranasally, orally, or by inhalation.

In addition, the present invention is intended to include any novel method of preparation of the compounds or formulations of the present invention.

In an additional embodiment, the invention provides a method to increase performance capability, alleviate a fatigue syndrome, and treat muscle damage and muscle degeneration comprising administering to the mammal, e.g., a human, a composition comprising recombinant human heat shock protein 70.

In another embodiment, the invention provides a method to increase performance capability, alleviate a fatigue syndrome, and treat muscle damage and muscle degeneration comprising administering to the mammal, e.g., a human, a composition comprising pegylated recombinant human heat shock protein 70. In certain embodiments, the recombinant human heat shock protein 70 shows a rate of clearance from serum that is at least an order of magnitude slower than unpegylated protein.

Without wishing to be bound by theory, in certain embodiments it is believed that HSP70 of the present invention may confer its action by stimulating proangiogenesis and activating satellite cells—a key population of the muscle stem cells.

IV. Formulations of the Invention

The formulations of the invention comprise HSP70, e.g., a therapeutically effective amount of HSP70, and may utilize any administration route that does not significantly impair the ability of the HSP70 to perform its intended function, e.g., intravenous injections, oral administration, nasal administration, intravaginal administration, rectal administration, or administration through inhalation.

As such, one embodiment of the invention provides a formulation comprising HSP70, e.g., a therapeutically effective amount of HSP70, and pharmaceutically acceptable carrier. In certain embodiments of the invention, the formulation comprising a compound of the invention is formulated for intravenous, subcutaneous, intranasal, oral, or inhalation administration.

In certain embodiments of the invention, the amount of the heat shock protein 70 present in the composition is in a range of 0.1 to 10 milligrams.

In certain embodiments of the invention, the HSP70 is recombinant human HSP70.

In certain embodiments of the invention, the HSP70 is pegylated HSP70, e.g., pegylated recombinant human HSP70, e.g., PEG-rhHSP70.

In certain embodiments, to prepare pharmaceutical formulations containing and HSP70 (e.g., PEG-rhHSP70) the HSP70 material, e.g., a therapeutically effective amount of the material, is admixed with a pharmaceutically acceptable carrier or excipient. Preferably the carrier or excipient is inert. A pharmaceutical carrier can be any compatible, non-toxic substance suitable for delivering the HSP70 formulations of the invention to a subject. Examples of suitable carriers include normal saline, Ringer's solution, dextrose solution, and Hank's solution. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. Formulations of the invention can be administered orally or injected into the body. Injections include but are not limited to intramuscular, subcutaneous, intradermal or intravenous. Alternatively, intra-articular injection or other routes could be used in appropriate circumstances. When administered parenterally, PEGylated HSP70 is preferably formulated in a unit dosage injectable form (solution, suspension, emulsion) in association with a pharmaceutical carrier. See, e.g., Avis et al., eds., Pharmaceutical Dosage Forms: Parenteral Medications, Dekker, N.Y. (1993); Lieberman et al., eds., Pharmaceutical Dosage Forms: Tablets, Dekker, N.Y. (1990); and Lieberman et al., eds., Pharmaceutical Dosage Forms: Disperse Systems, Dekker, N.Y. (1990). Alternatively, compositions of the invention may be introduced into a patient's body by implantable or injectable drug delivery system, e.g., Urquhart et al. Ann. Rev. Pharmacol. Toxicol. 24:199-236, (1984); Lewis, ed., Controlled Release of Pesticides and Pharmaceuticals, Plenum Press, New York (1981); U.S. Pat. Nos. 3,773,919; 3,270,960; and the like. The pegylated HSP70 can be administered in aqueous vehicles such as water, saline or buffered vehicles with or without various additives and/or diluting agents. Preparation of such pharmaceutical compositions is known in the art; see, e.g., Remington's Pharmaceutical Sciences and U.S. Pharmacopeia: National Formulary, Mack Publishing Company, Easton, Pa. (1984).

A. Administration of Formulations of the Present Invention

In general, however, the formulations of the invention that comprise HSP70 can be administered in a variety of dosage forms that do not affect or significantly detract from the increased stability of the HSP70 (i.e., allowing such formulations to achieve their desired function) including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form. The oral dosage form can be a tablet or a caplet. The formulations can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the formulations comprising the HSP70 are delivered to a desired site, such as the brain, by continuous injection via a shunt.

In another embodiment, the formulations of the invention can be administered parenterally, such as intravenous (i.v.) administration. The formulations for administration will commonly comprise a solution of HSP70 dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of HSP70 in these formulations can vary widely, and will be selected primarily based on fluid volumes, viscosities, body weight, and the like, in accordance with the particular mode of administration selected and the patient's needs. For i.v. administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, HSP70 can be administered by introduction into the central nervous system of the subject, e.g., into the cerebrospinal fluid of the subject. The formulations for administration will commonly comprise a solution of HSP70 dissolved in a pharmaceutically acceptable carrier. In certain aspects, HSP70 is introduced intrathecally, e.g., into a cerebral ventricle, the lumbar area, or the cisterna magna. In another aspect, HSP70 is introduced intraocularly, to thereby contact retinal ganglion cells.

The pharmaceutically acceptable formulations can be suspended in aqueous vehicles and introduced through conventional hypodermic needles or using infusion pumps. Prior to introduction, the formulations can be sterilized with, preferably, gamma radiation or electron beam sterilization.

For oral administration, the compounds will generally be provided in unit dosage forms of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include, but are not limited to sodium and calcium carbonate, sodium and calcium phosphate, and lactose, while corn starch and alginic acid are suitable disintegrating agents. Binding agents may include, but are not limited to starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of HSP70 with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active HSP70 doses.

For transmucosal administration (e.g., buccal, rectal, nasal, ocular, etc.), penetrants appropriate to the barrier to be permeated are used in the formulation. Such penetrants are generally known in the art.

In particular, formulations of the invention may be administered to the nasal cavity in any suitable form. For example, the formulations of the invention may be administered to the nasal cavity in the form of drops or a spray, or the powders of the invention may be administered in aerosolized form.

One method of administering the formulations of the invention would be to use a spray device. Spray devices can be single ("unit") dose or multiple dose systems, for example comprising a bottle, pump and actuator, and are available from various commercial sources, including Pfeiffer (Germany), Valois (France), Calmar (Germany), Ursatech (Germany), Bespak (UK) and Becton-Dickinson (USA). Electrostatic spray devices, such as described in U.S. Pat. No. 5,655,517, are also suitable for the intranasal administration of the formulations of the invention.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the HSP70 will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The suppositories for rectal administration of HSP70 can be prepared by mixing the drug with a suitable non-irritating excipient, which is solid at ordinary temperatures but liquid at the rectal temperatures and will therefore melt in the rectum to release the drug. Such materials are cocoa butter and polyethylene glycols.

The compounds can be delivered transdermally, by a topical route, formulated as applicator sticks, solutions, suspensions, emulsions, gels, creams, ointments, pastes, jellies, paints, powders, or aerosols.

The HSP70 may also be presented as aqueous or liposome formulations. Aqueous suspensions can contain HSP70 in admixture with excipients suitable for the manufacture of aqueous suspensions. Such excipients include, but are not limited to a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending HSP70 in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the HSP70 may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In general a suitable dose will be in the range of 0.001 to 10 mg per kilogram body weight of the recipient per day, preferably in the range of 0.005 to 1 mg per kilogram body weight per day. The desired dose is preferably presented once daily, but may be dosed as two, three, four, five, six or more sub-doses administered at appropriate intervals throughout the day.

The HSP70 can be administered as the sole active agent, or in combination with other known therapeutics to be beneficial in the treatment of related HSP70 disorders or conditions. In any event, the administering physician can provide a method of treatment that is prophylactic or therapeutic by adjusting the amount and timing of drug administration on the basis of observations of one or more symptoms of the disorder or condition being treated.

Details on techniques for formulation and administration are well described in the scientific and patent literature, see, e.g., the latest edition of Remington's Pharmaceutical Sciences, Maack Publishing Co, Easton Pa. ("Remington's"). After a pharmaceutical composition has been formulated in an acceptable carrier, it can be placed in an appropriate container and labeled for treatment of an indicated condition). For administration of the HSP70, such labeling would include, e.g., instructions concerning the amount, frequency and method of administration.

EXEMPLIFICATION

The present invention is illustrated by the following examples, which are not intended to be limiting in any way.

I. Synthetic Preparations of HSP70 and -HSP-70-PEG

Example 1

Fermentation of rhHSP70

To prepare sufficient amounts of HSP70, 5 L of he E. coli expression strain HMS 174 (DE3) hHSP70 may be grown in animal free medium containing 12 g phytone peptone, 60 g yeast extract, 40 g sodium chloride, 1 g methionine, and water to 5 liters. Before inoculation with expression strain bacteria, the medium may be sterilized, and supplemented with kanamycin to a final concentration of 30 mcg per milliliter. The medium may then be inoculated with one liter of an overnight culture of the HMS174(DE3) bacteria. The pH, level of dissolved oxygen and temperature inside the fermenter reactor may be carefully monitored. When the culture reaches an optical density of approximately 1.2 (for example, approximately 2.5 hours after inoculation), IPTG (isopropyl-B-D-thiogalactopyranoside) may be added to a final concentration of 1 mM to initiate the induction of expression of rhHSP70. Growth may then be continued until an optical density of approximately 2.7 is attained (for example, after an additional 3.5 hours following addition of IPTG). The fermented bacteria may then be harvested by centrifugation using standard techniques. The bacterial pellet may be re-suspended in 1 L of the 10 mmol PBS buffer (1 mmol EDTA, 10% glycerol). The re-suspended bacteria may then optionally be frozen on dry ice before further processing. To continue processing, the frozen bacteria may be thawed if necessary, and then may be disrupted by pressure lysis. The resulting lysate may then be cleared and sterile filtered.

Example 2

Purification of rhHSP70

A bacterial lysate comprising rhHSP70 may be subjected to the following two-step purification protocol. The specific example provided utilizes 500 mL of lysate; adjustments may be made for different lysate volumes. In the first step of the protocol, 500 mL of the cleared lysate, prepared as set forth above, may be diluted two-fold with 10 mM sodium phosphate buffer pH 7.0. This 1 L of diluted and cleared bacterial lysate may be loaded onto a of DEAE Sephacel (Pharmacia) column (13 cm×15 cm) previously equilibrated with 2 column volumes of buffer A (10 mM sodium phosphate buffer pH 7.0, 20 mM sodium chloride, 10 mM ammonium sulfate). The elution is carried out with two column volumes of buffer B (20 mM sodium phosphate buffer pH 7, 85 mM sodium chloride, 10 mM ammonium sulfate). About 2 L of eluate is expected for recovery. The eluate may then be diafiltered (buffer exchanged) against a 10-fold volume of buffer C (20 mM sodium citrate pH 6.0, 100 mM sodium chloride, 10 mM ammonium sulfate).

In the second step of the protocol, a 700 mL column (13 cm×5.5 cm) ATP agarose (Sigma-Aldrich) may be equilibrated in one column volume of buffer D (20 mM sodium citrate pH 6.0, 85 mM sodium chloride, 10 mM ammonium sulfate). And the diafiltered solution may be run over the ATP agarose column. The column may then be washed with six column volumes of buffer D and finally eluted with 2 column volumes of buffer E (20 mM sodium citrate pH 6.0, 100 mM sodium chloride, 10 mM ammonium sulfate, 1 mM magnesium acetate, 1 mM ATP). The eluted material, human rhHSP70 having a purity of greater than 95 percent may be buffer exchanged into phosphate buffered saline and concentrated to a final concentration of 10-20 mg/ml, and then sterile filtered.

Example 3

PEGylation Techniques

The efficacy of a therapeutic agent may be enhanced by improving its bioavailability via several means, one of which is PEGylation, a process of chemically linking polyethylene glycol (PEG) to the therapeutic agent of interest, with the resulting conjugate exhibiting an increased serum half-life. Additional advantages of the PEGylated products may also include lower immunogenicity, decreased dosing frequency, increased solubility, enhanced stability, and reduced renal clearance. Because the most common reactive sites on proteins (including peptides) for attaching PEG are the $\epsilon$ amino groups of lysine and the $\alpha$ amino group of the N-terminal residue, early methods of PEGylation resulted in modification of multiple sites, yielding not only monoPEGylated conjugates consisting of mixtures of positional isomers, such as PEGINTRON™ (Grace et al., J. Biol. Chem. 2005; 280:6327) and PEGASYS® (Dhalluin et al., Bioconjugate Chem. 2005; 16:504), but also adducts comprising more than one PEG chain.

The PEG reagents that are used to prepare PEGylated compounds of the invention may comprise a heterogenous mixture of PEGs having a different number (n) of ethylene glycol subunits in the PEG polymer. A single ethylene glycol subunit ($-(CH_2CH_2O)$) of PEG has a molecular weight of about 44 Daltons. Therefore, the molecular weight of the PEG polymer depends on the number (n). The PEGs attached to the PEGylated rhHSP70 compounds of the present invention will have n in the range from about 400 to about 1000 subunits. Preferably, the PEGs attached to the PEGylated HSP70 compounds of the present invention will have n in the range from about 400 to about 750.

A. Activated PEG for Amino or Imino Conjugation

To conjugate PEG to HSP70, an activated linker covalently attached to one or more PEG molecules may be reacted with an amino or imino group of an amino acid residue, e.g., with an alpha amino group at the N-terminus of HSP70, to form a PEG-HSP70 of the present invention.

A linker is "activated" if it is chemically reactive and ready for covalent attachment, e.g., to an amino group on an amino acid residue. Any activated linker can be used in this invention provided it can accommodate one or more PEG molecules and form a covalent bond, e.g., with an amino group of an amino acid residue under suitable reaction conditions. For example, the activated linker attaches to an alpha amino group in a highly selective manner over other attachment sites, e.g., epsilon amino group of lysine or imino group of histidine.

Activated PEG can be represented by the formula: $(PEG)_b$-L', where PEG covalently attaches to a carbon atom of the linker to form an ether bond, b is 1 to 9 (i.e. 1 to 9 PEG molecules can be attached to the linker), and L' contains a reactive group (an activated moiety) that can react with an amino or imino group on an amino acid residue to provide a covalent attachment of the PEG to HSP70.

In one embodiment, an activated linker (L') of the invention contains an aldehyde of the formula RCHO, where R is a linear (straight chain) or branched $C_{1-11}$ alkyl. After covalent attachment of an activated linker to HSP70, the linker (referred to as "-L-" in the structural formulas recited herein) between the HSP70 and PEG contains 2 to 12 carbon atoms. Propionaldehyde is an example of an activated linker of this invention. PEG-propionaldehyde, and is described in U.S. Pat. No. 5,252,714 and is commercially available from Shearwater Polymers (Huntsville, Ala); represented by the formula PEG-$CH_2CH_2CHO$.

In certain embodiments, a suitable activated branched (also known as "multi-armed") linker can be used. Any suitable branched PEG linker that covalently attaches two or more PEG molecules to an amino group on an amino acid residue of HSP70, e.g., to an alpha amino group at the N-terminus, can be used. A branched linker used in this invention may contain two or three PEG molecules. For example, a branched PEG linker used in this invention can be a linear or branched aliphatic group that is hydrolytically stable and contains an activated moiety, e.g., an aldehyde group, which reacts with an amino group of an amino acid residue, as described above. The aliphatic group of a branched linker may contain 2 to 12 carbons. For example, an aliphatic group can be a t-butyl which contains as many as three PEG molecules on each of three carbon atoms (i.e., a total of 9 PEG molecules) and a reactive aldehyde moiety on the fourth carbon of the t-butyl. Examples of activated, branched PEG linkers are also described in U.S. Pat. Nos. 5,643,575, 5,919,455, and 5,932,462. One having ordinary skill in the art, in light of the present invention, can prepare modifications to branched PEG linkers as desired, e.g., addition of a reactive aldehyde moiety.

Methods for the preparation of linkers for use in the present invention are well known in the art, e.g., see U.S. Pat. Nos. 5,643,575, 5,919,455, and 5,932,462. Activated PEG-linkers, such as PEG-aldehydes, can be obtained from a commercial source, e.g., Shearwater Polymers, (Huntsville, Ala.) or Enzon, Inc. (Piscataway, N.J.).

B. Conjugation Reaction Between PEG and HSP70 Amino or Imino Group

The following schematic illustrates a reaction between an activated PEG aldehyde linker and an amino or imino group of an amino acid residue of one of the HSP70 monomers: PEG-R—CHO+$NH_2$-HSP70$\leftrightarrows$PEG-R—CH=N-HSP70, where R is a $C_{1-11}$ alkyl and N is nitrogen of a reactive amino group on an amino acid residue of HSP70. In this reaction, the activated PEG covalently attaches to the HSP70 to form an imine linkage. Reduction of the imine linkage by the reducing agent, e.g., sodium cyanoborohydride (Sigma-Aldrich, St. Louis, Mo.) forms pegylated HSP70, as shown: PEG-R—CH=N-HSP70+$NaCNBH_3$→PEG-R—$CH_2$—NH-HSP70. Other reducing agents can be used instead of sodium cyanoborohydride in this reaction, including sodium borohydride, tertiary butyl amine borane, sodium triacetyl borohydide, dimethylamine borate, trimethylamine borate, and pyridine borate. Sodium cyanoborohydride is used in certain embodiments because it specifically reduces an imine linkage, which is formed between an aldehyde group of the activated PEG and amino group of the amino acid of HSP70.

As shown in the reactions, a Schiff base is formed during the preparation of PEG-HSP70. The concern that this intermediate, which is very difficult to separate from PEG-HSP70 and could lower the purity of the PEG-HSP70 if the intermediate accumulates in the reaction and is not reduced to the product, may be avoided by using higher concentrations of reducing agent, about 75:1 to 350:1 (e.g., Kinstler et al., Pharm. Res. 13:996-1002 (1996) and Chamow et al., Bioconjugate Chem. 5: 133-140 (1994)).

Various aqueous buffers can be used in the present method to catalyze the covalent addition of PEG to HSP70. The pH of a buffer used is from about 5.5 to 7.8, e.g., the pH is in a neutral range, e.g., from about 6.3 to 7.5. This neutral pH range would also increase the site-specific pegylation of HSP70 at the alpha amino group of the N-terminus versus other imino or amino groups of other amino acid residues, e.g., lysine or histidine. In certain embodiments, a buffers having a pKa close to neutral pH range is used, e.g., phosphate buffer.

The temperature range for preparing a PEG-HSP70 of the invention is from about 5° C. to 30° C. For example, in certain embodiments, the temperature is from about 18° C. to 25° C.

The pegylation reaction can proceed from 3 to 48 hours, e.g., 10 to 24 hours. The reaction can be monitored using SE (size-exclusion)-HPLC, which can distinguish HSP70, mono-PEG-HSP70 and di-PEG-HSP70 (i.e., pegylation occurs on two amino acid residues of HSP70), etc. At anytime when the desired HSP70 is obtained, the reaction can be terminated by adding glycine solution to quench any remaining activated PEG.

Conventional separation and purification techniques known in the art can be used to purify PEG-HSP70, such as size exclusion (e.g. gel filtration) and ion exchange chromatography.

It may be desirable to polish or resolve a population of PEG-HSP70 in a PEG-HSP70 composition prepared according to a method of the present invention. The polishing step separates less stable PEG-HSP70 (e.g. His-PEG-HSP70) from stable PEG-HSP70 (e.g. N-terminus-PEG-HSp70 or Lys-PEG-HSP70), and thus can achieve greater homogeneity of stable positional isomers, e.g., greater than 95% of a PEG-HSP70 composition. Less stable positional isomers of PEG-HSP70, e.g., histidine-PEG-HSP70, can be hydrolyzed during a polishing step. The population of PEG-HSP70 can be incubated in an aqueous buffer, e.g., a TRIS buffer (e.g., 10 to 300 mM, e.g., about 30 to 70 mM), at about pH 5.0 to 9.0, e.g., pH 7.0 to 8.0 at 15° C. at 35° C. overnight. Alternatively, the population of PEG-HSP70 can be treated with 0.05 to 0.4 M hydroxylamine HCl salt (pH about 6.5) at room temperature for 0.5 to 10 hours. Hydrolyzed HSP70 and PEG remnant can be removed from the population of stable PEG-HSP70 by a separation/purification step using, e.g., gel filtration or ion exchange chromatography.

In U.S. Pat. No. 5,985,265 the PEGylation of interferon using an aldehyde linker was accomplished at acidic pH 4.0 at 4° C. Conventional wisdom in the art teaches that for most activated PEG, as the reaction pH is increased under basic conditions pegylation occurs at more stable sites on the protein. For PEGylated IL-10 (U.S. Pat. No. 7,052,686), succinimidyl carbonate-PEG forms about 90% Lys-PEG-IL-10 (more stable) and about 10% His-PEG-IL-10 (less stable) at a reaction pH 8.8, and about 64% Lys-PEG-IL-10 and 36% His-PEG-IL-10 at a reaction pH 6.3.

C. Preparation of Cysteine Modified HSP70-PEG

In one embodiment, rhHSP70-PEG was prepared by using PEG-Maleimide-20 KDa reagent (Nanocs, N.Y., USA). The maleimide group reacted specifically with sulfhydryl groups when the pH of the reaction mixture was between pH 6.5 and 7.5; the result was formation of a stable thioether linkage that was not reversible (i.e., the bond cannot be cleaved with reducing agents). HSP70 has 5 cysteine groups in the following AA positions: 17, 267, 306, 574, and 603.

No cysteine thiols were known to participate in the formation of the intramolecular disulfide bonds and therefore all cysteines are potentially amenable to pegylation though in certain condition as Cys574 had been reported having a propensity for forming intermolecular disulfide bonds (Nemoto et al. 2006). From the structural consideration, Cys267, Cys306 could be buried in the middle of the protein and/or be masked by substrate making them less likely to be accessible. The Ellman test confirmed the presence of free thiol groups. However, when conducting the pegylation reaction in PBS buffer at pH 7.1, no changes in HPLC retention time were seen and subsequent SDS-PAGE gels did not reveal any reaction products but only a spot at 70 kDA for the unaltered HSP70.

After multiple trials, PEGylation only proceeded using denatured protein and the optimum conditions were in 6 M guanidine, whereas lower guanidine concentrations or using urea led to less efficient coupling. By varying the ratio of PEG-Maleimide the extent of cysteine pegylation was controlled, from an average of 1 to 5 PEG fragments per one protein molecule. Based on the HPLC data, a peak related to the starting protein vanishes when using a total of 50 eqv of PEG-maleimide. The final purification of HSP70-PEG is achieved by size exclusion chromatography in PBS at pH 7.4.

Pegylated protein products refolded rapidly when diluted in PBS or during a passage through the size-exclusion column. For in vivo experiment pegylated products were concentrated using an Amicon membrane (cutoff 4 kDa) to a concentration of 0.5-2 mg/ml (as determined by micro BCA) and passed through a 0.22 micron filter. The biological activity of the HSP70-PEG molecules was confirmed by the ATP-ase test using a commercial kit (ENZO Life Sciences, Farmingdale, N.Y.). Different co-factors, e.g., HSP40 and modified albumins, have been reported to improve the test response; however, the most robust results were received in 1 mmol ADP.

II. In Vivo Applications

Example 4

Application of the rhHSP70 for Increased Performance Capability Experienced During Intense Physical Exercise The goal of this experiment was to study the role of exogenous rhHSP70 in experimental model of intense physical exercise in healthy adult wild white male rats (180-220 g, "Rappolovo" animal facility) and its effect on increased endurance. rhHSP70 was used in two doses of 50 and 100 mcg per animal injected intraperitoneally in 1 ml of water. The experiment was conducted in 3 groups of animals: 6 animals (control, placebo injection), 6 animals (50 mcg HSP70), 6 animals (100 mcg HSP70). Experimental animals were pre-selected from the group that passed an initial fitness and training test: a daily run on a treadmill for 5 min repeated for 3 consecutive days (treadmill rate 20 m/min, attack angle 20°). The study treadmill test was run to exhaustion (termination of the running routine by an animal) for a total of 9 sessions that were repeated every second day, at the same time of the day. HSP70 was administered 5-6 min following the completion of the test for the first 6 sessions. The observed animal running time was used as a measure of endurance capability (FIG. 1, Table 1).

TABLE 1

Variations in performance (time of exercise to exhaustion) relative to the result of the first exercise session.

| Exercise Session No. | Days of Observation | Animal Groups | | |
|---|---|---|---|---|
| | | Control | HSP70, 50 mcg | HSP70, 100 mcg |
| 1 | 1 | 100 | 100 | 100 |
| 2 | 3 | 105.6 ± 5.9 | 108.6 ± 4.8 | 113.0 ± 4.0 |
| 3 | 5 | 106.2 ± 3.0 | 115.1 ± 5.9 | 119.0 ± 4.8* |
| 4 | 8 | 109.9 ± 4.2 | 124.1 ± 5.1* | 127.3 ± 5.2* |

TABLE 1-continued

Variations in performance (time of exercise to exhaustion) relative to the result of the first exercise session.

| Exercise Session No. | Days of Observation | Animal Groups | | |
|---|---|---|---|---|
| | | Control | HSP70, 50 mcg | HSP70, 100 mcg |
| 5 | 10 | 81.2 ± 3.7 | 111.7 ± 3.5* | 113.9 ± 3.4* |
| 6 | 12 | 61.9 ± 4.4 | 104.2 ± 5.9* | 121.5 ± 5.3* |
| 7 | 15 | 55.6 ± 4.9 | 97.3 ± 3.0* | 114.6 ± 4.6* |
| 8 | 17 | 47.7 ± 4.0 | 62.2 ± 3.3* | 87.0 ± 4.0* |
| 9 | 19 | 46.7 ± 3.1 | 61.1 ± 4.1* | 82.2 ± 3.8* |

Note:
*statistically significant ($p \leq 0.05$) compared to control

A statistically significant differentiation in the endurance capability was seen during the 3rd training session: the control group and low-dose HSP70 animals were shown to have results similar to the training session No. 1, whereas the high-dose HSP70 animals demonstrated improved endurance (FIG. 1). In all the subsequent training sessions, the HSP70-treated animal outperformed a control group in a dose-dependent manner.

Starting from the training session No. 5, the performance/endurance in all groups began to decrease. However, the trend was slower in the HSP70-treated animals. After termination of the HSP70 administration following the training session No. 6, the endurance capability has further decreased, however, in each training session the animal receiving HSP70 outperformed untreated animals, by as much as 35.5% in the 100 mcg group in the last training session No. 9.

As a result of the exhaustion following the exercise on the day 19, the control group demonstrated increased levels of blood proteins, creatinine, as well as sodium and potassium as compared with both treated groups (Table 2). Additionally, treated animals displayed decreased activity of the creatinine kinase and lactate dehydrogenase (LDG) that may indicate cytoprotective properties of the HSP70. Importantly, we detected no anabolic effects of HSP70—there was no additional body mass increase in treated group as compared to the control group though all animals demonstrated slightly elevated body mass at the end of the experiment.

TABLE 2

Blood biochemistry results following completion of the study (day 19).

| Test | Units | Animal Groups | | |
|---|---|---|---|---|
| | | Control | HSP70, 50 mcg | HSP70, 100 mcg |
| Proteins | g/L | 72.5 ± 1.7 | 63.6 ± 1.1* | 66.0 ± 1.6* |
| Creatinine | mmol/L | 67.7 ± 3.1 | 52.0 ± 3.5* | 56.3 ± 1.4* |
| Uric Acid | mmol/L | 9.1 ± 1.2 | 8.6 ± 0.7 | 9.7 ± 0.4 |
| Glucose | mmol/L | 7.2 ± 0.5 | 6.6 ± 0.2 | 6.6 ± 0.8 |
| $K^+$ | mmol/L | 6.6 ± 0.3 | 6.8 ± 0.2 | 7.3 ± 0.2 |
| $Na^+$ | mmol/L | 149.4 ± 0.9 | 144.2 ± 0.5* | 145.2 ± 0.5* |
| $Ca^{2+}$ | mmol/L | 2.50 ± 0.03 | 2.46 ± 0.05 | 2.46 ± 0.01 |
| $Cl^-$ | mmol/L | 112.2 ± 0.9 | 107.8 ± 1.2* | 109.8 ± 0.3* |
| Creatinine kinase | IU/L | 13368.0 ± 455.3 | 10668.4 ± 312.0* | 8954.5 ± 826.4* |
| LDG | IU/L | 6245.7 ± 260.4 | 3146.8 ± 227.2* | 2407.8 ± 241.2* |

Note:
*statistically significant ($p \leq 0.05$) compared to control

Microscopy Analysis

Figure 2:
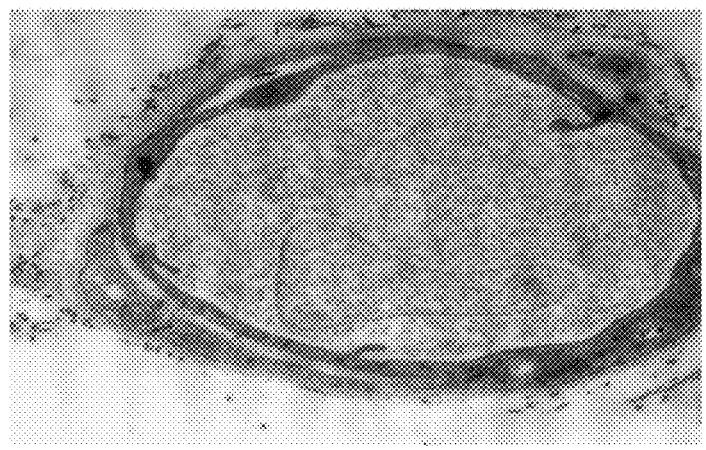
FIG. 2 depicts muscle electron microscopy (×15000) from the control (untreated) animal. Clearly visible is myofibrils separation and edema, capillary edema, and damaged erythrocytes (shadows) as manifestation of the rhabdomyolysis. An activated podocyte is located in the upper left corner.
Figure 3:
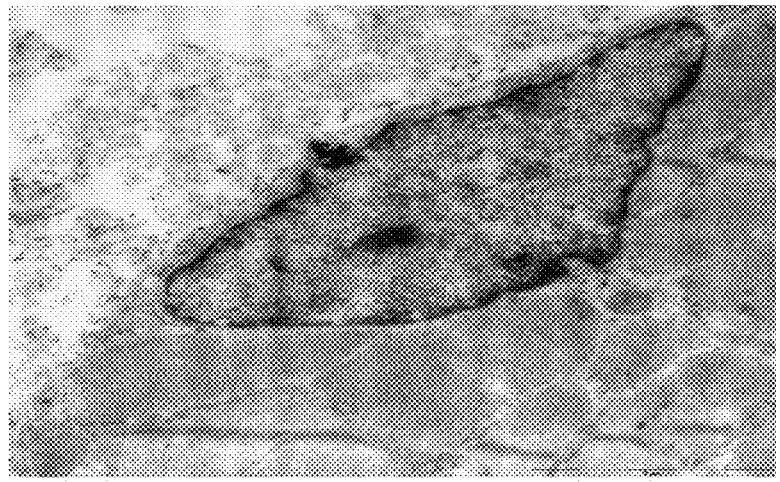
FIG. 3 depicts muscle electron microscopy (×15000) from the treated animal (HSP70, 100 mcg). The view is dominated by an activated satellite cell with a large euchromatin-rich nucleus.
Figure 4:
FIG. 4 depicts muscle electron microscopy (×15000) from the treated animal (HSP70-PEG, 100 mcg). The view is dominated by an activated satellite cell and numerous mitochondria.
Figure 5:
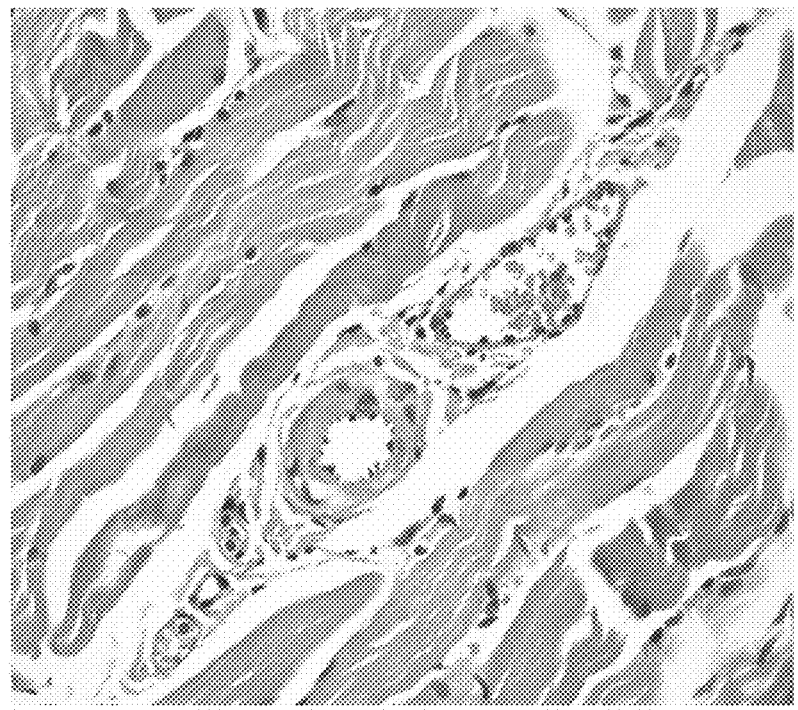
FIG. 5 depicts muscle optical microscopy (×400) from the treated animal (HSP70, 100 mcg). Zones of the neoangiogenesis are clearly visible with partial myofibrils separation.
Figure 6:
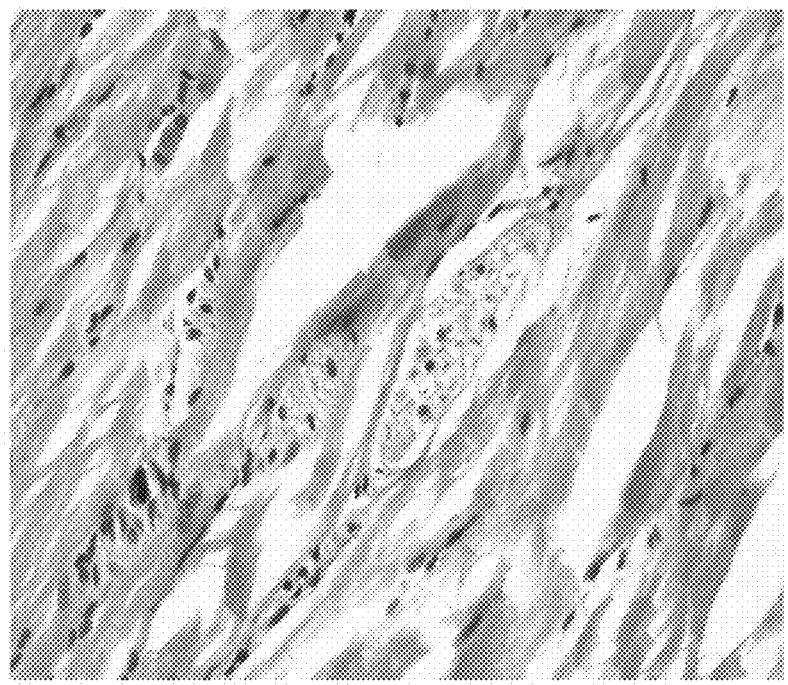
FIG. 6 depicts muscle optical microscopy (×400) from the treated animal (HSP70-PEG, 100 mcg). Zones of the neoangiogenesis with large lymphocytes are clearly visible with partial myofibrils separation.

To confirm the findings from the physiological functional testing and blood biochemistry, a limb muscle biopsy was conducted in the sacrificed animals following a completion of the study. Transmission electron microscopy was carried out on a JEOL 110 CX and Hitachi H-300 electron microscopes using samples fixed by 2.5% glutaric aldehyde with subsequent treatment in PBS solution of the osmium tetraoxide and dewatering in alcohol/acetone (FIG. 2-4). Tissue slices were generated using Ultracut-Reichert microtome. The Mallory staining for optical microscopy was done with eosin and hematoxylin (FIG. 5,6).

In all the groups structural alterations were detected indicative of a muscle dystrophy, rhabdomyolysis and inflammation that was less pronounced in the treated groups. An activation of angiogenesis is known to be strongly associated with muscle regeneration (Borselli et al., 2010), with a capillary network being an important indication of the recovery processes. Correspondingly, in HSP70-treated animals, a significant dose-dependent increase was found in the density of the capillary vessels, by 170-330%, from 275/$mm^2$ in the control group to 907/$mm^2$ in the high-dose HSP70 treated group (Table 3).

Additionally, staining was performed for the satellite cells, an adult stem cell population associated with myofibers and localized within the basal lamina of the muscle fibers that are believed to be primarily responsible for muscle regeneration (Wagers et al., 2005). A 6-8 times increase was observed in the density of the satellite cells in the HSP70-treated versus untreated animals (Table 3).

TABLE 3

Capillary density and satellite cells count following completion of the exercise study.

| Parameter | Animal Groups | | |
|---|---|---|---|
| | Control | HSP70 (100 mcg) | HSP70-PEG (100 mcg) |
| Capillary density (per mm²) | 275.0 ± 21.2 | 907.5 ± 37.4* | 990 ± 37.4* |
| Satellite cells (% control) | 100 | 680.2 ± 150.3* | 840.1 ± 170.4* |

Note:
*statistically significant ($p \leq 0.05$) compared to control

Example 5

Application of the rhHSP70-PEG for Increased Performance Capability Experienced during Intense Physical Exercise The goal of this experiment was to study the role of exogenous rhHSP70-PEG in experimental model of intense physical exercise in healthy adult wild white male rats (180-220 g, "Rappolovo" animal facility) and its effect on increased endurance. rhHSP70-PEG was used in a dose of 100 mcg per animal injected intraperitoneally in 1 ml of water. The experiment was conducted in 3 groups of animals: 6 animals (control, placebo injection), 6 animals (100 mcg HSP70), 6 animals (100 mcg HSP70-PEG). Experimental animals were pre-selected from the group that passed an initial fitness and training test: a daily run on a treadmill for 5 min repeated for 3 consecutive days (treadmill rate 20 m/min, attack angle 20°). The study treadmill test was run to exhaustion (termination of the running routine by an animal) for a total of 10 sessions that were repeated every day, at the same time of the day. HSP70 and HSP70-PEG were administered 5-6 min following the completion of the test on the daily basis. The observed animal running time was used as a measure of performance capability (Table 4).

There was no significant difference between the groups in the first five training sessions. After that, a ca. 30% drop was observed in the exercise time for the control and subsequent decrease in the follow-up sessions, to ca. 50% of the capacity at the end of the experiments. In contrast, treated groups displayed a gradually increased performance reaching 115-125% as compared to the beginning of the study. HSP70-PEG showed a statistically significant performance improvement over HSP70. This observation was corroborated by the higher density of the capillary vessels and satellite cells count (Table 3).

Notably, we again detected no anabolic effects of HSP70 or HSP70-PEG (Table 5)—there was no additional body mass increase in treated group as compared to the control group though all animals demonstrated slightly elevated body mass at the end of the experiment (Table 5).

TABLE 4

Variations in performance (time of exercise to exhaustion) relative to the result of the first exercise session for HSP70-PEG.

| Exercise session/day | Animal Groups | | |
|---|---|---|---|
| | Control | HSP70 (100 mcg) | HSP70-PEG (100 mcg) |
| 1 | 100 | 100 | 100 |
| 2 | 105.3 ± 6.0 | 104.9 ± 6.8 | 103.4 ± 1.2 |
| 3 | 109.9 ± 5.4 | 103.1 ± 6.6 | 104.6 ± 7.7 |
| 4 | 106.8 ± 8.5 | 119.1 ± 2.9 | 109.9 ± 5.5 |
| 5 | 101.7 ± 6.6 | 112.9 ± 4.8 | 115.0 ± 1.8 |
| 6 | 86.9 ± 9.1 | 115.9 ± 5.2* | 117.0 ± 2.1* |
| 7 | 56.1 ± 7.9 | 123.8 ± 3.8* | 121.2 ± 5.6* |
| 8 | 68.7 ± 4.1 | 119.2 ± 2.8* | 123.4 ± 3.6* |
| 9 | 60.2 ± 1.7 | 117.0 ± 4.6* | 125.1 ± 1.9* |
| 10 | 54.8 ± 5.3* | 115.6 ± 3.6* | 124.3 ± 6.7* |

Note:
*statistically significant ($p \leq 0.05$) compared to control

TABLE 5

Body mass change (g) in the course of exercise routine.

| Exercise Session | Animal Groups | | |
|---|---|---|---|
| | Control | HSP70-PEG (100 mcg) | HSP70-PEG (100 mcg) |
| 1 | 161.7 ± 6.9 | 162.2 ± 7.7 | 161.0 ± 7.8 |
| 2 | 166.3 ± 7.7 | 184.3 ± 7.1 | 179.3 ± 3.5 |
| 3 | 168.0 ± 7.8 | 187.0 ± 7.1 | 183.0 ± 3.9 |
| 4 | 171.8 ± 8.2 | 190.0 ± 6.8 | 187.3 ± 4.5 |
| 5 | 174.3 ± 8.2 | 189.8 ± 7.4 | 189.3 ± 4.1 |
| 6 | 174.2 ± 8.7 | 189.8 ± 6.0 | 188.0 ± 2.9 |
| 7 | 174.8 ± 8.9 | 192.5 ± 5.6 | 189.3 ± 3.6 |
| 8 | 178.5 ± 8.7 | 195.2 ± 4.8 | 184.0 ± 4.3 |
| 9 | 182.5 ± 8.8 | 198.2 ± 4.6 | 195.0 ± 3.7 |
| 10 | 182.2 ± 8.6 | 196.0 ± 4.2 | 199.7 ± 4.1 |

Example 6

Clinical Use of HSP70 for Treatment of the Acquired Muscle Myopathy

Figure 7:
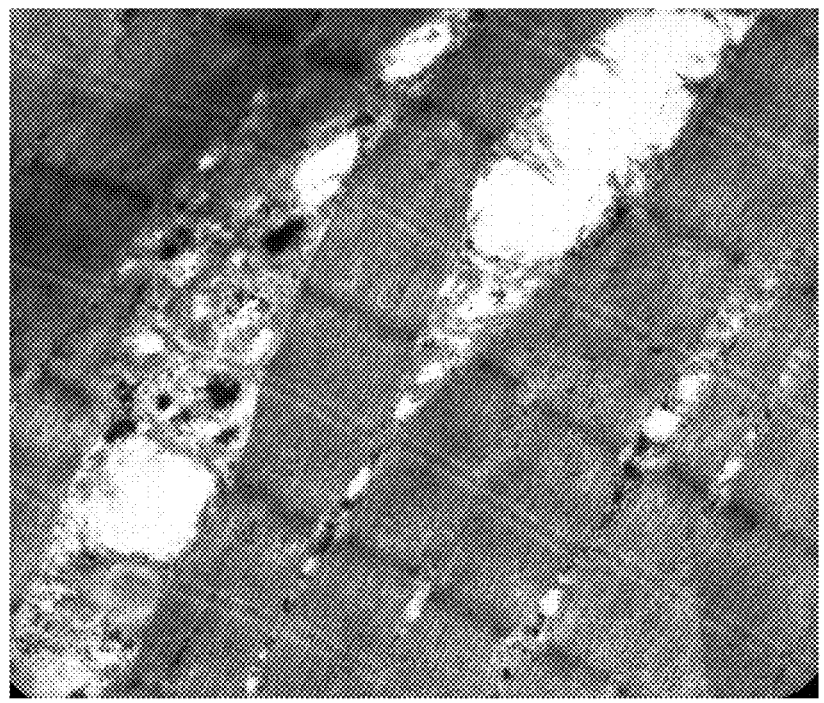
FIG. 7 depicts muscle electron microscopy (×15000) of the patient before the treatment with HSP70. Muscle damage is manifested in a formation of the vacuoles, delamination of the myofibrils and formation of the glycogen aggregates in between the myofibrils.

Subject X, a 62 year old human patient suffered from a significant body mass loss (35 kg over a period of 1 year), muscle atrophy of the lower extremities and upper body, decrease in the muscle power and endurance, muscle contractures. Electron microscopy (FIG. 7) of the biopsy from musculus brachialis and gastrocnemius revealed significant rhabdomiolysis, mitochondrial damage with a formation of numerous vacuoles, and reduction in the number of satellite cells. The clinical diagnosis was established in Saint Petersburg (Russia) Military Medical Academy as an acquired mitochondrial myopathy and resulting cachexia.

HSP70 was then administered IV, 0.5 mg per dose over a period of 7 days.

Figure 8:
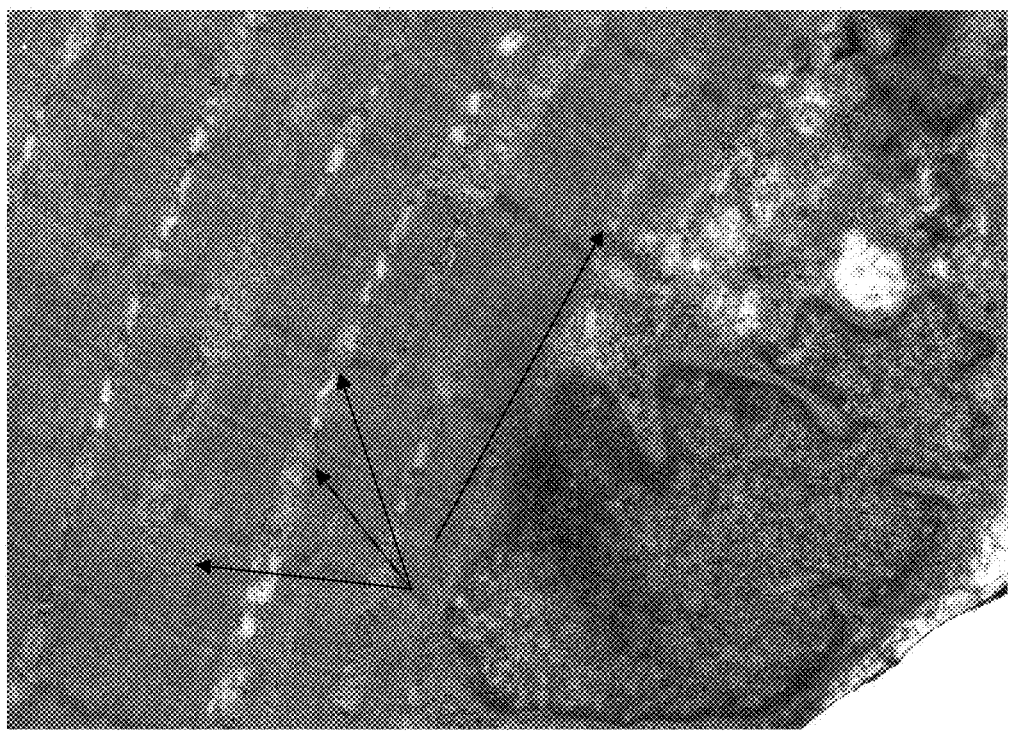
FIG. 8 depicts muscle electron microscopy (×15000) of the patient after the treatment with HSP70. Muscle regeneration is manifested in improved cross-section, and activated myocyte nuclear function.

Analysis following the 6 weeks subsequent to the last administration of HSP70 showed that the patient's body mass had increased by 6.5 kg, which was associated with increased muscle strength. In addition, the electron microscopy (FIG. 8) revealed significant reduction in the myofibril delamination and their improved cross-section, restoration of the mitochondrial structure and activation of the myocyte nuclear function.

REFERENCES

Borselli C, Storrie H, Benesch-Lee F, Shvartsman D, Cezar C, Lichtman J W, Vandenburgh H H, Mooney D J.

Functional Muscle Regeneration with Combined Delivery of Angiogenesis and Myogenesis Factors. Proc. Natl. Acad. Sci. U.S.A. 2010, 107(8):3287-92.

Gehrig S M, van der Poel C, Sayer T A, Schertzer J D, Henstridge D C, Church J E, Laron S, Russell A P, Davies K E, Febbraio M A, Lynch G S. Hsp72 Preserves Muscle Function and Slows Progression of Severe Muscular Dystrophy, Nature. 2012, 484(7394):394-8.

Jammes Y, Steinberg J G, Delliaux S, Bregeon F, Chronic Fatigue Syndrome Combines Increased Exercise-Induced Oxidative Stress And Reduced Cytokine and HSP Responses, J. Intern. Med. 2009, 266(2), 196-206.

Kärkkäinen A M, et al. Vascular Endothelial Growth Factor-D transgenic Mice Show Enhanced Blood Capillary Density, Improved Postischemic Muscle Regeneration, and Increased Susceptibility to Tumor Formation, Blood, 2009, 113:4468-4475.

Lee C E, McArdie A, Griffiths R D, The Role of Hormones, Cytokines and Heat Shock Proteins During Age-Related Muscle Loss, Clin. Nutr. 2007, 26(5):524-34.

Levenberg S, et al. Engineering Vascularized Skeletal Muscle Tissue, Nature Biotechnol. 2005, 23:879-884.

Maglara A A, Vasilaki A, Jackson M J, McArdle A, Damage to Developing Mouse Skeletal Muscle Myotubes in Culture: Protective Effect of Heat Shock Proteins, J. Physiol. 2003, 548(3):837-846.

Messina S, et al. (2007) VEGF Overexpression via Adeno-Associated Virus Gene Transfer Promotes Skeletal Muscle Regeneration and Enhances Muscle Function in mdx Mice, FASEB J. 2007, 21:3737-3746

Morton J P, Kayani A C, McArdle A, Drust B, Exercise-Induced Stress Response of Skeletal Muscle, with Specific Emphasis on Humans, Sport Med. 2009, 39(8): 643-662.

Nemoto T K Fukuma Y, Itoh H, Takagi T A, Ono T. Disulfide Bridge Mediated by Cysteine 574 Is Formed in the Dimer of the 70-kDa Heat Shock Protein, J. Biochem. 2006, 139: 677-687.

Panossian A, Wikman G, Evidence-Based Efficacy of Adaptogens in Fatigue, and Molecular Mechanisms Related to Their Stress-Protective Activity. Curr. Clin. Pharmacol. 2009, 4(3):198-219.

Shiota M, Kusakabe H, Izumi Y, Hikita Y, Nakao T, Funae Y, Miura K, Iwao H, Heat Shock Cognate Protein 70 Is Essential for Akt Signaling in Endothelial Function, Arterioscler. Thromb. Vasc. Biol. 2010, 30:491-497.

Silva E A, Mooney D J, Spatiotemporal Control of Vascular Endothelial Growth Factor Delivery from Injectable Hydrogels Enhances Angiogenesis, J Thromb Haemost. 2007, 5:590-598.

Slepian M J, Massia S P, Treatment of Tissues to Reduce Subsequent Response to Injury. U.S. Pat. No. 5,914,345.

Srivastava P K, Chandawarkar R Y, Compositions and Methods for Promoting Tissue Repair Using Heat Shock Proteins. US Patent Application US 2003/0012793.

Takahashi N., Heat Shock Protein Inducer. U.S. Pat. No. 6,846,845 B2.

Vigh, L, Literáti P N, Horváth I, Török Z, Balogh G, Glatz A, Kovács E, Boros I, Ferdinándy P, Farkas B, Jaszlits L, Jednákovits A, Korányi L, Maresca B. Bimoclomol: a Nontoxic, Hydroxylamine Derivative with Stress Protein-Inducing Activity and Cytoprotective Effect, Nature Medicine, 1997, 3(10):1150-1154.

Wagers A J, Conboy I M, Cellular and Molecular Signatures of Muscle Regeneration: Current Concepts and Controversies in Adult Myogenesis, Cell 2005, 122:659-667.

Whitham M, Fortes M B, Heat Shock Protein 72: Release and Biological Significance, Front. Biosci. 2008, 13:1328-1339.

Incorporation by Reference

The entire contents of all patents, published patent applications and other references cited herein are hereby expressly incorporated herein in their entireties by reference.

Equivalents

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A method of treating a subject with muscle damage due to physical exercise comprising administering to the subject an amount of HSP70 effective for increasing muscle performance in the subject.

2. The method of claim 1, wherein the HSP70 is human heat shock protein 70.

3. The method of claim 1, wherein the HSP70 is pegylated HSP70.

4. The method of claim 1, wherein the subject is human.

5. The method of claim 1, wherein the HSP70 is administered intravenously, subcutaneously, intranasally, orally, or by inhalation.

* * * * *